United States Patent [19]

Foster et al.

[11] Patent Number: 4,902,710
[45] Date of Patent: Feb. 20, 1990

[54] SEROTONIN AND NOREPINEPHRINE UPTAKE INHIBITORS

[75] Inventors: Bennie J. Foster, Greenwood; David C. Hunden, Carmel; Edward R. Lavagnino, Indianapolis, all of Ind.

[73] Assignee: Eli Lilly and Company, Indianapolis, Ind.

[21] Appl. No.: 284,501

[22] Filed: Dec. 14, 1988

[51] Int. Cl.$^4$ ............ A61K 31/38; A61K 31/34; C07D 409/00; C07D 333/32
[52] U.S. Cl. .................. 514/438; 514/336; 514/343; 514/351; 514/369; 514/372; 514/422; 514/424; 514/444; 514/461; 514/649; 546/280; 546/281; 546/283; 546/284; 546/300; 548/189; 548/213; 548/517; 548/527; 548/550; 549/59; 549/60; 549/65; 549/472; 549/479; 564/341
[58] Field of Search ........... 514/336, 343, 351, 369, 514/372, 422, 424, 438, 444, 461, 649; 546/280, 281, 283, 284, 300; 548/189, 213, 517, 527, 550; 549/59, 60, 65, 472, 479; 564/341

[56] References Cited

U.S. PATENT DOCUMENTS

| 4,018,895 | 4/1977 | Molloy et al. ............... 424/330 |
| 4,194,009 | 3/1980 | Molloy et al. ............... 424/330 |
| 4,314,081 | 2/1982 | Molloy et al. ............... 564/347 |
| 4,329,356 | 5/1982 | Holland ........................ 424/274 |
| 4,686,309 | 8/1987 | Barriere et al. ............. 564/355 |

FOREIGN PATENT DOCUMENTS 273658  7/1988  European Pat. Off. .
2060618 5/1981  United Kingdom .

OTHER PUBLICATIONS

Wolff, *Burger's Medicinal Chemistry*, Part III, 4th ed., pp. 1008, 1014-1017, 1038-1039 and 1041-1043 (1981).

*Primary Examiner*—Alan Siegel
*Attorney, Agent, or Firm*—Douglas J. Taylor; Leroy Whitaker

[57] ABSTRACT

The present invention provides propanamines, substituted at the 3-position of the propanamine chain with a thio, sulfinyl or sulfonyl moiety, which are capable of selectively inhibiting the uptake of serotonin and norepinephrine.

27 Claims, No Drawings

SEROTONIN AND NOREPINEPHRINE UPTAKE INHIBITORS

BACKGROUND OF THE INVENTION

U.S. Pat. Nos. 4,018,895, 4,194,009, and 4,314,081 disclose 3-aryloxy-3-phenylpropanamines as being potent, selective, blockers of the uptake of certain monoamines. For example, the hydrochloride salt of fluoxetine (dl-N-methyl-γ-[4-(trifluoromethyl)phenoxy]benzenepropanamine) is a selective serotonin (5-hydroxytryptamine) uptake inhibitor useful in the treatment of depression, anxiety, obesity, and other disorders. Similarly, tomoxetine hydrochloride ((−)-N-methyl-γ-(2-methylphenoxy)benzenepropanamine hydrochloride) is a selective inhibitor of norepinephrine uptake currently undergoing clinical investigation for antidepressant activity.

An object of this invention is to provide certain propanamines, substituted at the 3-position with a thio, sulfinyl or sulfonyl moiety, which are also potent, selective inhibitors of both serotonin and norepinephrine uptake.

SUMMARY OF THE INVENTION

The present invention provides propanamines which are substituted at the 3-position of the propanamine chain with a thio, sulfinyl or sulfonyl group. The compounds are potent, selective, serotonin and norepinephrine uptake inhibitors.

More specifically, the present invention relates to a compound of the formula

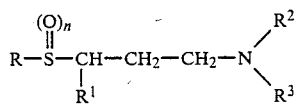

wherein:
- R is phenyl, substituted phenyl, naphthyl, substituted naphthyl, thienyl, halothienyl, ($C_1$-$C_4$ alkyl)-substituted-thienyl, furanyl, halofuranyl, ($C_1$-$C_4$ alkyl)-substituted-furanyl, pyrrolyl, halopyrrolyl or ($C_1$-$C_4$ alkyl)-substituted-pyrrolyl;
- $R^1$ is phenyl, substituted phenyl, $C_5$-$C_7$ cycloalkyl, thienyl, halothienyl, ($C_1$-$C_4$ alkyl)-substituted-thienyl, furanyl, pyridyl or thiazolyl;
- $R^2$ and $R^3$ are each independently hydrogen or methyl;
- n is 0, 1 or 2; and
- the pharmaceutically acceptable acid addition salts thereof.

The invention also provides pharmaceutical formulations comprising a compound of the above formula and a pharmaceutically acceptable carrier, diluent, or excipient therefor. Further embodiments of the invention are methods for selectively inhibiting the uptake of serotonin and norepinephrine, as well as for treating a variety of disorders which have been linked to decreased neurotransmission of serotonin and norepinephrine in mammals including obesity, depression, alcoholism, pain, loss of memory, anxiety, smoking, and the like, employing a compound of the invention.

DETAILED DESCRIPTION OF THE INVENTION

In the above formula, the term "substituted phenyl" represents a phenyl ring which is substituted with one or two substituents independently selected from halo, $C_1$-$C_4$ alkyl, $C_1$-$C_3$ alkoxy, trifluoromethyl or $C_2$-$C_4$ alkenyl. The substituents may be located at any position of the phenyl ring.

When R is naphthyl, it can be either 1-naphthyl or 2-naphthyl. When R is substituted naphthyl, it can be either 1-naphthyl or 2-naphthyl monosubstituted, at any available position of the naphthyl ring system, with a substituent selected from halo, $C_1$-$C_4$ alkyl or trifluoromethyl.

When R or $R^1$ are thienyl, they can be either 2-thienyl or 3-thienyl. When R or $R^1$ are furanyl, they can be either 2-furanyl or 3-furanyl. When R is pyrrolyl, it can be either 2-pyrrolyl or 3-pyrrolyl.

($C_1$-$C_4$ Alkyl)-substituted-thienyl, -furanyl or -pyrrolyl represent thienyl, furanyl or pyrrolyl rings which are monosubstituted with a $C_1$-$C_4$ alkyl substituent. Typical ($C_1$-$C_4$ alkyl)-substituted-thienyl, -furanyl or -pyrrolyl groups include 4-methyl-2-thienyl, 3-ethyl-2-thienyl, 2-methyl-3-thienyl, 4-propyl-3-thienyl, 5-n-butyl-2-thienyl, 4-methyl-3-thienyl, 3-methyl-2-thienyl, 4-ethyl-2-furanyl, 2-isopropyl-3-furanyl, 5-methyl-2-furanyl, 3-propyl-2-furanyl, 4-t-butyl-3-furanyl, 2-propyl-3-pyrrolyl, 5-isobutyl-2-pyrrolyl, 4-methyl-2-pyrrolyl, 2-methyl-3-pyrrolyl and the like.

Halothienyl, halofuranyl or halopyrrolyl represent thienyl, furanyl or pyrrolyl rings which are monosubstituted with a halo substituent. Typical halothienyl, halofuranyl or halopyrrolyl groups include 3-chloro-2-thienyl, 4-bromo-3-thienyl, 2-iodo-3-thienyl, 5-iodo-3-thienyl, 4-fluoro-2-thienyl, 2-bromo-3-thienyl, 4-chloro-2-thienyl, 3-bromo-2-furanyl, 5-chloro-2-furanyl, 4-iodo-3-furanyl, 2-fluoro-3-furanyl, 5-bromo-3-furanyl, 4-chloro-3-pyrrolyl, 2-iodo-3-pyrrolyl, 5-fluoro-2-pyrrolyl, 4-bromo-2-pyrrolyl and the like.

When $R^1$ is pyridyl, it can be either 2-pyridyl, 3-pyridyl or 4-pyridyl. When $R^1$ is thiazolyl, it can be either 2-thiazolyl, 4-thiazolyl or 5thiazolyl.

The above formula and associated definitions use the terms "$C_1$-$C_4$ alkyl", "$C_1$-$C_3$ alkoxy", "$C_2$-$C_4$ alkenyl" and "halo". The term "$C_1$-$C_4$ alkyl" represents a straight or branched alkyl chain bearing from one to four carbon atoms. Typical $C_1$-$C_4$ alkyl groups include methyl, ethyl, n-propyl, isopropyl, n-butyl, isobutyl, sec-butyl and t-butyl. The term "$C_1$-$C_3$ alkoxy" represents methoxy, ethoxy, propoxy or isopropoxy. The term "$C_2$-$C_4$ alkenyl" represents ethylene, propylene, isopropylene, 1-butene and 2-butene. Finally, the term "halo" represents chloro, fluoro, bromo and iodo.

While all of the compounds of the present invention are believed to inhibit the uptake of serotonin and norepinephrine in mammals, certain of these compounds are preferred for such uses. Preferred compounds are those wherein R is phenyl, substituted phenyl, naphthyl, substituted naphthyl, thienyl or ($C_1$-$C_4$ alkyl)-substituted-thienyl; $R^1$ is phenyl; and n, $R^2$ and $R^3$ are as defined above. Further preferred compounds are those wherein R, $R^1$, $R^2$ and $R^3$ are as above and n is 0.

Even more preferred compounds of the present invention are those wherein R is phenyl, phenyl substituted with methyl, methoxy or trifluoromethyl, thienyl or methyl-substituted-thienyl and $R^1$, $R^2$ and $R^3$ and n are as above. Expecially preferred compounds are those wherein R, $R^1$ and n are as above, $R^2$ is hydrogen and $R^3$ is methyl.

The most preferred compounds of the invention are N-methyl-3-[(2-methylphenyl)thio]benzenepropanamine, N-methyl-3-[(2-methoxyphenyl)thio]benzenepropanamine, N-methyl-3-[[4-(trifluoromethyl)phenyl]thio]benzenepropanamine, and N-methyl-3-(2-thienylthio)benzenepropanamine.

The compounds of the present invention possess an asymmetric carbon atom represented by the carbon atom labeled in the following formula

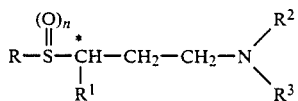

As such, the compounds can exist as individual stereoisomers as well as a racemic mixture. Accordingly, the compounds of the present invention include not only the racemates, but also their respective optically active d- and l-isomers. Unless otherwise indicated all compounds named herein are intended to exist as racemic mixtures.

The invention also includes pharmaceutically acceptable acid addition salts of the compounds defined by the above formula. Since the compounds of this invention are amines, they are basic in nature and accordingly react with any number of inorganic and organic acids to form pharmaceutically acceptable acid addition salts. Since the free amines of the invention are typically oils at room temperature, it is preferable to convert the free amines to their corresponding pharmaceutically acceptable acid addition salts, which are routinely solid at room temperature, for ease of handling.

Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, hydrochloride, hydrobromide, hydroiodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, p-toluenesulfonate, naphthalene-2-sulfonate, mandelate and the like salts. Preferred pharmaceutically acceptable acid addition salts include those formed with organic acids such as oxalic acid, maleic acid, and para-toluenesulfonic acid, and especially those formed with mineral acids such as hydrochloric acid and hydrobromic acid.

The following compounds further illustrate compounds contemplated within the scope of the present invention:

3-(phenylthio)benzenepropanamine
3-(phenylthio)-3-(2-methyl-3-thienyl)propanamine
3-[(3-chloro-2-thienyl)thio]-3-(3-bromophenyl)propanamine
3-(2-naphthylsulfinyl)-3-(2-pyridyl)propanamine
3-[(2-methyl-3-pyrrolyl)sulfonyl]-3-cyclohexylpropanamine
3-(2-furanylthio)-3-(5-thiazolyl)propanamine
N-methyl-3-[(2-propylphenyl)thio]benzenepropanamine
N-methyl-3-[1-(4-trifluoromethyl)naphthylthio]-3-(3-furanyl)propanamine
N-methyl-3-(2-naphthylthio)-3-[(2-bromo-4-chloro)phenyl]propanamine
N-methyl-3-[(4-propoxyphenyl)thio)]-3-(3-t-butyl-2-thienyl)propanamine
N-methyl-3-(3-thienylsulfinyl)-3-cyclopentylpropanamine
N-methyl-3-[(4-bromo-2-thienyl)thio)-3-(4-pyridyl)propanamine
N-methyl-3-[(2-ethyl-3-thienyl)sulfonyl]benzenepropanamine
N-methyl-3-(3-furanylsulfinyl)-3-(4-ethenylphenyl)propanamine
N-methyl-3-[(5-chloro-2-furanyl)thio]-3-(3-methylphenyl)propanamine
N-methyl-3-[(4-propyl-3-furanyl)sulfonyl]-3-cycloheptylpropanamine
N-methyl-3-(2-pyrrolylthio)-3-(4-ethoxyphenyl)propanamine
N-methyl-3-[(2-fluoro-3-pyrrolyl)sulfonyl]benzenepropanamine
N-methyl-3-[(5-methyl-3-pyrrolyl)thio]-3-(5-thiazolyl)propanamine
N,N-dimethyl-3-(phenylsulfinyl)-3-(2-chloro-3-thienyl)propanamine
N,N-dimethyl-3-[(2-ethylphenyl)thio]-3-(4-methyl-2-thienyl)propanamine
N,N-dimethyl-3-[(2-chloro-4-methylphenyl)thio]benzenepropanamine
N,N-dimethyl-3-[1-naphthylthio]-3-(2-furanyl)propanamine
N,N-dimethyl-3-[(1-propyl-2-naphthyl)sulfonyl]-3-(4-trifluoromethylphenyl)propanamine
N,N-dimethyl-3-(2-thienylsulfinyl)benzenepropanamine
N,N-dimethyl-3-[(5-bromo-3-thienyl)thio]-3-(4-pyridyl)propanamine
N,N-dimethyl-3-[(4-t-butyl-2-thienyl)sulfonyl]-3-cyclohexylpropanamine
N,N-dimethyl-3-(2-furanylthio)-3-(3,5-dichlorophenyl)propanamine
N,N-dimethyl-3-[(2-bromo-3-furanyl)thio]benzenepropanamine
N,N-dimethyl-3-[(4-ethyl-2-furanyl)sulfonyl]-3-(2-thiazolyl)propanamine
N,N-dimethyl-3-(2-pyrrolylsulfinyl)-3-(5-ethyl-2-thienyl)propanamine
N,N-dimethyl-3-[(4-chloro-3-pyrrolyl)thio]-3-(2-ethyl-4-methylphenyl)propanamine
N,N-dimethyl-3-[(2-methyl-3-pyrrolyl)thio]-3-(2-chloro-6-methylphenyl)propanamine
3-[(4-chlorophenyl)thio]-3-(2-methylphenyl)propanamine oxalate
3-(2-naphthylsulfonyl)-3-(2-thienyl)propanamine
3-[(2-ethyl-3-thienyl)thio]-3-(4-trifluoromethylphenyl)propanamine benzoate
N-methyl-3-[(3,5-dibromophenyl)sulfinyl]benzenepropanamine tartrate
N-methyl-3-[(2-methyl-3-furanyl)thio]-3-cyclohexylpropanamine lactate
N-methyl-3-[(4-chloro-2-thienyl)thio]-3-(3-pyridyl)propanamine phenylpropionate N-methyl-3-[(4-propyl-3-pyrrolyl)sulfinyl]-3-(2-methoxyphenyl)propanamine glycollate
N-methyl-3-[(1-ethyl-2-naphthyl)sulfonyl]-3-(4-trifluoromethylphenyl)propanamine acetate
N-methyl-3-[(2-ethoxyphenyl)thio]-3-(4-ethyl-3-thienyl)propanamine phosphate
(+)-N-methyl-3-[(4-chloro-2-naphthyl)thio]-3-cyclopentylpropanamine
(−)-N-methyl-3-[(2-methylphenyl)sulfonyl]-3-(2-thiazolyl)propanamine
(+)-N-methyl-3-[(2-fluoro-3-furanyl)sulfinyl]benzenepropanamine
(−)-N-methyl-3-[(5-isobutyl-3-pyrrolyl)thio]-3-(2,6-dimethylphenyl)propanamine
(+)-N-methyl-3-[(5-n-butyl-2-thienyl)thio]-3-(2-propoxyphenyl)propanamine
(−)-N-methyl-3-(phenylthio)-3-(2-chloro-3-thienyl)-propanamine
(+)-N-methyl-3-[(4-chloro-2-pyrrolyl)sulfinyl]-3-(3-ethylphenyl)propanamine
(−)-N-methyl-3-(1-naphthylthio)-3-(4-ethyl-3-thienyl)-propanamine
(+)-N-methyl-3-(3-pyrrolylsulfonyl)-3-(4-methoxyphenyl)propanamine malonate
(−)-N-methyl-3-[(2,4-diethylphenyl)thio]-benzenepropanamine bisulfate
(+)-N-methyl-3-[(4-iodo-2-thienyl)thio]-3-cyclohexylpropanamine hydrobromide
(−)-N-methyl-3-[(4-t-butyl-3-pyrrolyl)sulfinyl]-3-(2-chlorophenyl)propanamine fumarate
N,N-dimethyl-3-[(3,5-dimethylphenyl)sulfinyl]-benzenepropanamine citrate
N,N-dimethyl-3-[(2-methyl-3-pyrrolyl)thio]-3-cyclopentylpropanamine succinate
N,N-dimethyl-3-[(4-isopropyl-2-thienyl)thio]-3-(3-pyridyl)propanamine xylenesulfonate
N,N-dimethyl-3-[(4-propylphenyl)sulfinyl]-3-(2-methoxyphenyl)propanamine maleate
N,N-dimethyl-3-[(3-chloro-2-naphthyl)sulfonyl]-3-(4-trifluoromethylphenyl)propanamine decanoate
N,N-dimethyl-3-[3,5-difluorophenyl)thio]-3-(4-methyl-3-thienyl)propanamine dihydrogenphosphate
(+)-N,N-dimethyl-3-[2-naphthylthio]benzene propamine
(−)-N,N-dimethyl-3-[(2-methylphenyl)sulfonyl]-3-(5-thiazolyl)propanamine
(+)-N,N-dimethyl-3-[(2-propyl-3-furanyl)sulfonyl]-3-3-cycloheptylpropanamine
(−)-N,N-dimethyl-3-[(5-isobutyl-3-thienyl)thio]-3-(2,6-diethylphenyl)propanamine
(+)-N,N-dimethyl-3-[(5-n-butyl-2-furanyl)sulfinyl]-3-(2-methoxyphenyl)propanamine
(−)-N,N-dimethyl-3-(phenylthio)benzenepropanamine
(+)-N,N-dimethyl-3-[(4-chloro-2-pyrrolyl)thio]-3-(3-ethoxyphenyl)propanamine
(−)-N,N-dimethyl-3-(1-naphthylthio)-3-(3-thienyl)-propanamine
(+)-N,N-dimethyl-3-(3-pyrrolylsulfonyl)-3-(2,6-dimethoxyphenyl)propanamine hydrochloride
(−)-N,N-dimethyl-3-[(2,4-diethylphenyl)thio]-3-(2-chlorophenyl)propanamine chlorobenzoate
(+)-N,N-dimethyl-3-[(3-bromo-2-thienyl)thio]-3-cyclohexylpropanamine suberate
(−)-N,N-dimethyl-3-[(4-methyl-3-pyrrolyl)sulfinyl]-3-(3-pyridyl)propanamine methanesulfonate The 3-thiopropanamines (compounds wherein n is 0) of the invention may be prepared according to the process of Reaction Scheme I, below.

Reaction Scheme I

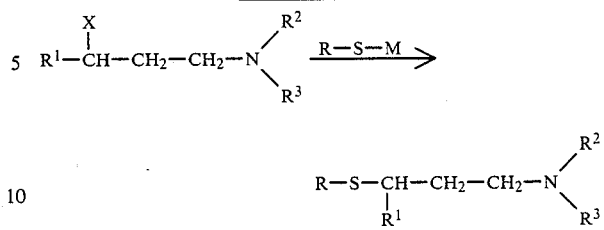

wherein R–R$^3$ are as defined previously;
X is halo; and
M is a group IA alkali metal.

In Reaction Scheme I, a suitably substituted 3-halopropanamine is reacted with an alkali metal salt of an appropriately substituted mercaptan to provide the corresponding 3-thiopropanamine of the invention. The reactants are preferably used in approximately equimolar quantities relative to each other. However, either reactant can be used in excess quantities, if desired.

The above reaction is preferably conducted in an inert solvent. Inert solvents which may be used include alcohols such as methanol, ethanol, isopropanol and the like, aromatic solvents such as benzene, toluene and the like, ethers such as diethyl ether, tetrahydrofuran and the like, or alkanes such as pentane, hexane, heptane or the like. The reaction is substantially complete after about 30 minutes to about 48 hours when conducted at a temperature in the range of from about 0° C. to about 150° C.

The product thiopropanamine may be isolated using standard isolation techniques. Typically, the reaction solution containing the thiopropanamine is concentrated by removing the inert solvent by distillation. The resulting residue is dissolved in a water immiscible solvent such as diethyl ether, ethyl acetate, chloroform and the like, and the resulting solution is washed with water and dried. Following distillation of the organic solvent, the isolated product may be further purified, if desired, by standard techniques such as crystallization from common solvents, or chromatography over solid supports such as silica gel or alumina.

The 3-sulfinyl and 3-sulfonylpropanamines (compounds wherein n is 1 or n is 2, respectively) of the invention can be prepared by reacting a suitably substituted 3-halopropanamine with an alkali metal salt of an appropriately substituted sulfinic acid, or a monooxygenated derivative thereof, in a manner analogous to that discussed above in Reaction Scheme I. The products may be isolated as previously described.

Alternatively, the 3-sulfinylpropanamines of the present invention can be prepared by oxidizing the corresponding 3-thio compound using any one of a number of methods known in the art. The oxidizing agent used is not critical. Typically, the oxidizing agent will be a peroxy acid derivative, such as paregoric acid, peracetic acid, m-chloroperbenzoic acid and the like; a positive halogen source, such as t-butylhypochlorite, N-bromosuccinimide, N-chlorosuccinimide, 1-chlorobenzotriazole and the like; an "active" MnO$_2$ source such as potassium permanganate and the like; or hydrogen peroxide. The oxidizing agent generally is employed in approximately equimolar quantities relative to the thiopropanamine. However, a slight molar excess, for example up to about 25%, of the oxidizing agent may be employed, if desired. When a strong oxidizing agent, for example a peroxy acid derivative or hydrogen peroxide, is employed, approximately equimolar quantities of the agent relative to the thiopropanamine should be used in order to minimize oxidation of the amine nitrogen atom.

The oxidation reaction is preferably conducted in an inert solvent, for example methylene chloride, chloroform, acetone, methanol, ethyl acetate and the like. When selecting the inert solvent, care should be taken to ensure that the oxidizing agent employed is compatible, from a safety standpoint, with the solvent selected. The reaction is substantially complete after about 30 minutes to about 48 hours when conducted at a temperature in the range of about $-20°$ C. to about 75° C. To prevent overoxidation to the 3-sulfonyl derivative, it is frequently desirable to use temperatures in the range of from about $-20°$ C. to about room temperature (24° C.). The product 3-sulfinylpropanamines may be isolated and purified as described above.

The 3-sulfonylpropanamines of the present invention can, alternatively, be prepared by oxidizing the corresponding 3-thio or 3-sulfinyl compounds in a manner analogous to the oxidation reaction described above. When the sulfonyl is prepared using a thiopropanamine starting material, the 3-sulfinyl compound is an intermediate. Again, the oxidizing agent used is not critical. Oxidizing agents which can be used include hydrogen peroxide, m-chloroperbenzoic acid, potassium permanganate, sodium dichromate, t-butyl hypochlorite and the like. When the sulfonyl is prepared by oxidation of the corresponding thio analog, at least two equivalents of the oxidizing agent per equivalent of thiopropanamine must be used. If a strong oxidizing agent is employed to prepare the sulfonyl, excessive amounts (i.e., amounts greater than the one or two equivalents of agent needed to convert the sulfinyl or thio starting material, respectively, to the sulfinyl) should be avoided in order to minimize oxidation of the amine nitrogen atom.

Compounds of the present invention wherein $R^2$ and $R^3$ are both methyl may, alternatively, be synthesized by reacting a primary amine compound of the invention ($R^2$ and $R^3$ are both hydrogen) with an excess of formaldehyde in the presence of sodium cyanoborohydride and a mutual solvent.

Compounds of the present invention wherein one of $R^1$ and $R^2$ is methyl and the other is hydrogen may, alternatively, be prepared by reacting a primary amine compound of the invention with ethyl chloroformate in the presence of triethylamine and a suitable solvent to provide the corresponding carbamate intermediate, which is then reduced in the presence of a suitable reducing agent, such as lithium aluminum hydride, to provide the N-methyl compounds of the present invention.

The compounds of the present invention wherein one of $R^1$ and $R^2$ is methyl and the other is hydrogen may also be prepared by demethylating the corresponding N,N-dimethyl substituted compound. Preferably, a reagent such as phenyl chloroformate, trichloroethyl chloroformate, or cyanogen bromide is reacted with the dimethylated compound to provide an intermediate, which is then hydrolyzed in a base to yield a compound of this invention in which one of $R^1$ and $R^2$ is methyl and the other is hydrogen.

As noted above, the optically active isomers of the racemates of the invention are also considered part of this invention. Such optically active isomers may be prepared from their respective optically active precursors by the procedures described above, or by resolving the racemic mixtures. This resolution can be carried out in the presence of a resolving agent, by chromatography or by repeated crystallization. Particularly useful resolving agents include dibenzoyl-d- and -l-tartaric acids and the like.

The pharmaceutically acceptable acid addition salts of the invention are typically formed by reacting a 3-thio, sulfinyl or sulfonylpropanamine of the invention with an equimolar or excess amount of a pharmaceutically acceptable acid. The reactants generally are combined in a mutual solvent such as acetone, diethyl ether or benzene. The salt normally precipitates out of solution within about 1 hour to about 10 days, and can be isolated by filtration.

The alkali metal salts of an appropriately substituted mercaptan, or the more highly oxidized analogs thereof, employed as starting materials in synthesizing the compounds of the invention are either commercially available, known in the literature, or can be prepared by methods known in the art. The other starting material employed in preparing the compounds of the invention; namely, the suitably substituted 3-halopropanamines, can be prepared according to the process of Reaction Scheme II, below.

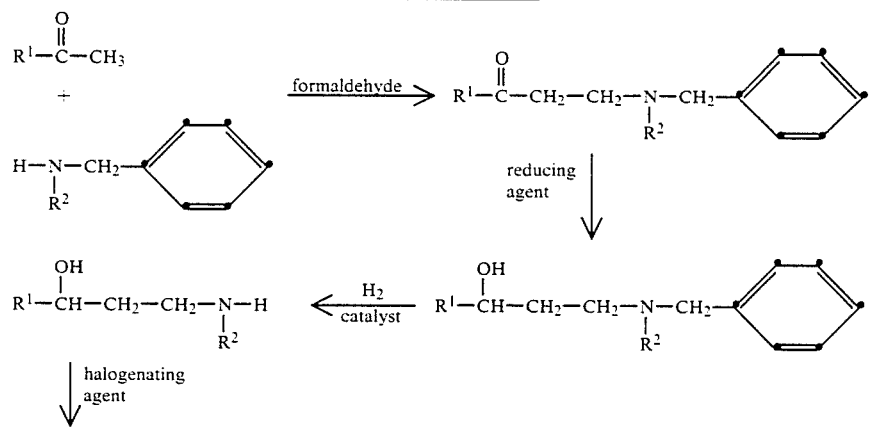

-continued

Reaction Scheme II

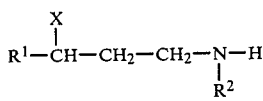

wherein $R^1$, $R^2$ and X are as previously defined.

In Reaction Scheme II, formaldehyde, benzylamine (or its N-methylated analog) and an appropriately substituted ketone are reacted in a Mannich reaction to form a 3-[(phenylmethyl)amino]-1-substituted-1-propanone. The keto function of the propanone is then reduced to an alcohol using a reducing agent, such as lithium aluminum hydride, sodium borohydride or the like, to provide a substituted α-[2-[(phenylmethyl)amino]ethyl]methanol. The phenylmethylamino moiety is then reduced using catalytic hydrogenation to yield a substituted α-(2-aminoethyl)methanol. Finally, the 3-halopropanamine starting materials used to prepare the compounds of the invention are obtained by converting the hydroxy group of the aminoethylmethanol to a halo group using a halogenating agent. Suitable halogenating agents which may be used include halogen acids such as hydrochloric acid, hydrobromic acid and the like and inorganic acid halides such as thionyl halide, phosphorus trihalide, phosphorus pentahalide and the like.

The above process can be used to produce starting materials wherein at least one of $R^2$ and $R^3$ is hydrogen. Starting materials wherein both $R^2$ and $R^3$ are methyl may be prepared according to the process of Reaction Scheme III, below.

Reaction Scheme III

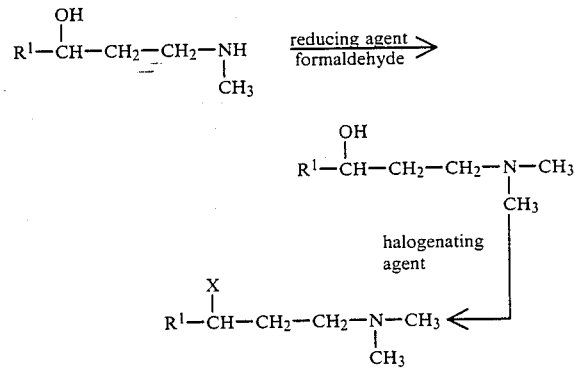

wherein $R^1$ and X are as previously defined.

In Reaction Scheme III, formaldehyde, an appropriately substituted α-[2-(methylamino)ethyl]methanol (prepared according to the procedure of Reaction Scheme II) and a reducing agent are reacted to provide the corresponding dimetyyl derivative. Suitable reducing agents which may be used are well known in the art and include such agents as hydrogen and a catalyst, zinc, hydrochloric acid, sodium borohydride and formic acid. Once the second methyl group is added, the N,N-dimethyl-3-halopropanamine starting material is readily prepared by converting the hydroxy group to a halogen group in the same manner as previously described.

The following Examples further illustrate the compounds of the present invention and methods for their synthesis. The Examples are not intended to be limiting to the scope of the invention in any respect and should not be so construed.

Preparation 1

N-Methyl-3-chloro-benzenepropanamine hydrochloride

To a five liter, 3-necked, round bottom flask equipped with two condensers were added 558.0 g (4.6 mol) methylbenzylamine and 500 ml of ethanol. The solution was stirred while an ethanolic solution of hydrochloric acid (170.0 g of acid dissolved in 2500 ml of ethanol) was added over a one hour period. After hydrochloric acid addition was complete, acetophenone (552.5 g; 4.6 mol) and paraformaldehyde (207.0 g; 6.9 mol) were added. The solution was heated until the liquid began to reflux and then stirred at that temperature overnight. The next morning an additional 137.0 g (4.6 mol) of paraformaldehyde were added and the reaction solution was stirred for an additional five hours at the reflux temperature. The solution was then cooled to room temperature (24° C.) and the solids which precipitated were collected by filtration, washed with ethanol and dried in a vacuum oven at 40° C. to provide 1090.0 g (82.0% yield) of 3-[methyl(phenylmethyl)amino]-1-phenyl-1-propanone hydrochloride.

A part of the above product (289.0 g; 1.0 mol) was charged into a 2-liter, 3-necked, round bottom flask containing 280 ml of isopropanol and 240 ml of water. Eighty grams of a 50%, by weight, sodium hydroxide solution were added over a 15 minute period. Sodium borohydride (10.0 g; 0.27 mol) was then added over a 10 minute period. The resulting solution was stirred at room temperature (24° C.) for about two hours. After two hours, 500 ml of methanol and an additional 10.0 g (0.27 mol) of sodium borohydride were added and the solution was stirred at room temperature (24° C.) over the weekend.

The reaction solution was concentrated by distilling approximately two-thirds of the solvent under reduced pressure. Methylene chloride and water were added to the remaining liquid. The resulting aqueous layer was separated from the organic layer and extracted three times with methylene chloride. The organic layer was combined with the methylene chloride extracts and the resulting solution was washed twice with water, dried over sodium carbonate, and then concentrated under reduced pressure to provide 253.0 g of α-[2-[methyl(phenylmethyl)amino]ethyl]benzenemethanol as an oil.

A portion of the above product (224.5 g; 0.88 mol) was dissolved in 1700 ml of 3A ethanol. Seventyfive grams of a 5% Palladium on carbon catalyst were added and the mixture was placed in a pressure reactor. The reactor was pressured to 60 psig using hydrogen gas and the reaction mixture was stirred overnight at room temperature (24° C.). The next morning the reactor was vented to atmospheric pressure and the catalyst removed by filtration. The solvent was distilled under reduced pressure to provide 140.0 g of α-[2-(methylamino)ethyl]benzenemethanol as an oil.

The above product was added to a 3-liter, 4-necked, round bottom flask containing 1000 ml of methylene chloride. Hydrochloric acid gas was passed through the solution for approximately 30 minutes. Thionyl chloride (108.0 g; 0.9 mol) was added and the resulting solution stirred at room temperature (24° C.) for three hours. Hexane (1000 ml) was then added and the solution stirred over the weekend, during which time a white solid precipitated. This solid was collected by filtration and dried in a vacuum oven at 40° C., in the presence of sodium hydroxide pellets, to provide the title compound.

F.D. mass spec.: 184

Analysis calculated for $C_{10}H_{15}NCl_2$; Theory: C, 54.56; H, 6.87; N, 6.36; Found: C, 54.46; H, 7.12; N, 6.55.

EXAMPLE 1

N-Methyl-3-[(2-methoxyphenyl)thio]benzenepropanamine hydrochloride

N-Methyl-3-chloro-benzenepropanamine hydrochloride (13.14 g, 0.06 mol) from Preparation 1 was dissolved in cold (0° C.) water. A 25%, by weight, sodium hydroxide solution (9.6 g of solution; 0.06 mol of sodium hydroxide) was also chilled to 0° C. Both solutions were added to a 100 ml separatory funnel containing 50 ml of toluene. The contents of the funnel were shaken and the layers allowed to separate. The aqueous layer was separated from the organic layer and then extracted with toluene followed by diethyl ether. The organic layer was combined with the organic extracts and the resulting solution was washed with a saturated brine solution, then dried over sodium carbonate, to provide an organic solution containing the free base of the compound of Preparation 1.

To a 250 ml round bottom flask, having a condenser, were added 100 ml of methanol and 2.0 g (0.05 mol) of sodium hydroxide pellets. 2-Methoxybenzenethiol (7.0 g, 0.05 mol) was added dropwise over a ten minute period, after which the resulting solution was heated until the liquid began to reflux. The solution was stirred at that temperature for about 15 minutes.

The organic solution of N-methyl-3-chlorobenzenepropanamine, prepared above, was added to the 250 ml flask. The resulting solution was heated until the liquid began to reflux and then stirred at that temperature overnight. The next morning the solution was cooled to room temperature (24° C.) and the solvents removed under reduced pressure to provide an oil. The oil was dissolved in a diethyl ether/water mixture. The resulting organic layer was separated from the aqueous layer, dried over sodium sulfate, and the solvent removed under reduced pressure to provide an oil.

The oil was dissolved in 200 ml of diethyl ether. Hydrochloric acid gas was passed through the solution for a period of about 15 minutes. Solids precipitated and were recovered by filtration. The solids were dissolved in hot (35° C.) methylene chloride. Hexane was added, the methylene chloride distilled, and solids again precipitated. These solids, recrystallized from methylene chloride-ethyl acetate, were dried in a vacuum oven at 60° C. to provide 13.0 g of N-methyl-3-[(2-methoxyphenyl)thio]benzenepropanamine hydrochloride, m.p. =130° C.

Analysis calculated for $C_{17}H_{22}NOSCl$; Theory: C, 63.04; H, 6.85; N, 4.32; Found: C, 63.61; H, 7.03; N, 4.83.

In an analogous manner to that described in Example 1, the following compounds were prepared:

EXAMPLE 2

N-Methyl-3-[(2-methylphenyl)thio]benzenepropanamine hydrochloride

N-Methyl-3-chloro-benzenepropanamine hydrochloride (13.14 g, 0.06 mol), 25%, by weight, sodium hydroxide solution (9.6 g of solution; 0.06 mol of sodium hydroxide), sodium hydroxide pellets (2.0 g, 0.05 mol) and 2-methylbenzenethiol (6.2 g, 0.05 mol) were reacted to provide N-methyl-3-[(2-methylphenyl)thio]benzenepropanamine as an oil. The oil was purified by preparative HPLC and then converted to the hydrochloride salt as in Example 1. Recrystallization from methylene chloride:ethyl acetate provided approximately 3.0 g of title compound. m.p. ≈90° C.

Analysis calculated for $C_{17}H_{22}NSCl$; Theory: C, 66.32; H, 7.20; N, 4.55; Found: C, 66.50; H, 7.10; N, 4.68.

EXAMPLE 3

N-Methyl-3-[[4-(trifluoromethyl)phenyl]thio]benzenepropanamine hydrochloride

N-Methyl-3-chloro-benzenepropanamine hydrochloride (13.14 g, 0.06 mol), 25%, by weight, sodium hydroxide solution (9.6 g of solution; 0.06 mol of sodium hydroxide), sodium hydroxide pellets (2.0 g, 0.05 mol and 4-trifluoromethylbenzenethiol (8.3 g, 0.05 mol) were reacted to provide N-methyl-3-[[4-(trifluoromethyl)phenyl]thio]benzenepropanamine as an oil. The oil was dissolved in 200 ml diethyl ether and hydrochloric acid gas was passed through the solution for about 15 minutes. The solvent was removed under reduced pressure to provide an oil which was dissolved in a 1:1:1 ethyl acetate:diethyl ether:hexane solvent mixture. The solvents were slowly removed under reduced pressure and crystals precipitated. The crystals were purified by preparing a slurry of the crystals partially dissolved in a 1:1:1 methylene chloride:ethyl acetate:diethyl ether solvent system. The mixture was chilled to 0° C. and the solids were recovered by filtration to provide 13.0 g of title compound. m.p. =125°–130° C.

Analysis calculated for $C_{17}H_{19}NSClF_3$; Theory: C, 56.43; H, 5.29; N, 3.87; Found: C, 56.65; H, 5.19; N, 3.96.

EXAMPLE 4

N-Methyl-3-[[4-(trifluoromethyl)phenyl]sulfinyl]benzenepropanamine hydrochloride One gram (2.77 mmol) of the compound of Example 3 was dissolved in 10 ml of methylene chloride. m-Chloroperbenzoic acid (0.57 g, 3.3 mmol) was also dissolved in 10 ml of methylene chloride. Both solutions were combined and the resulting solution stirred overnight at room temperature (24° C.). The next morning a saturated sodium carbonate solution was added to precipitate unreacted m-chloroperbenzoic acid. The precipitate was removed by filtration and the filtrate concentrated to a viscous oil by removing the solvent under reduced pressure.

The oil was dissolved in diethyl ether. Hydrochloric acid gas was passed through the solution for about 15 minutes. Hexane was added to the acidic diethyl ether solution and solids precipitated, which were recovered by filtration.

Five hundred milligrams of the recovered solids were purified by reverse phase chromatography using a 35:65 acetonitrile:water mixture. The solution containing purified product was concentrated to approximately onethird of its original volume and the pH adjusted to about 10.0 with ammonium hydroxide. The basic solution was extracted three times with 25 ml of diethyl ether. The ether extracts were combined and dried over sodium sulfate. Hydrochloric acid gas was passed through the solution for about 15 minutes and solids precipitated. The solids, isolated by removing the solvent under reduced pressure, were identified as N-methyl-3-[[4-trifluoromethyl)phenyl]sulfinyl]benzenepropanamine hydrochloride. m.p. ≈ 135° C.

Analysis calculated for $C_{17}H_{19}NOSClF_3$; Theory: C, 54.04; H, 5.07; N, 3.71; Found: C, 54.28; H, 5.33; N, 3.58.

EXAMPLE 5

N-Methyl-3-[[4-(trifluoromethyl)phenyl]sulfonyl]benzenepropanamine hydrochloride To a 250 ml round bottom flask were added 0.75 g (2 mmol) of the compound of Example 3, 100 ml of water and 3.75 g of "OXONE" (sold by DuPont; 1 part potassium sulfate, 1 part potassium bisulfate and 2 parts potassium peroxy monosulfate). The solution was allowed to stand at room temperature (24° C.) for 3 hours and then an additional 3.75 g of "OXONE" were added. The resulting solution was allowed to stand over the weekend, while an oily layer formed in the bottom of the reaction flask.

The pH of the two-phase mixture was adjusted to about 8.0 using a 50%, by weight, sodium hydroxide solution. The oil layer was isolated from the aqueous layer by extracting the two-phase mixture with ethyl acetate followed by methylene chloride. The extracts were combined, washed with a saturated sodium chloride solution, and then dried over sodium sulfate. The solution was concentrated to an oil by solvent removal under reduced pressure. The oil was dissolved in diethyl ether and a saturated solution of hydrochloric acid dissolved in diethyl ether was added. A fine, white, solid precipitated, which was recovered by filtration and washed with diethyl ether. The solid was air dried to provide 100 mg of title compound.

FD mass spec.: 357

EXAMPLE 6

N-Methyl-3-(2-thienylthio)benzenepropanamine hydrochloride

N-Methyl-3-chloro-benzenepropanamine hydrochloride (12.0 g, 0.055 mol) was dissolved in 10 ml of cold (0° C.) water. A 50%, by weight, sodium hydroxide solution (4.36 g of solution, 0.055 mol of NaOH) was added to the aqueous solution. The resulting solution was extracted three times with diethyl ether and the ether extracts were combined, then dried over sodium carbonate.

To a 250 ml, 3-necked, round bottom flask, having a condenser, were added 4.2 g (0.05 mol) of thiophene, 50 ml of hexane and 30 ml of diethyl ether. The solution was heated until the solvent began to reflux, at which time 21 ml of a 1.6M solution of n-butyllithium dissolved in hexane were added dropwise over a period of 15 minutes. After n-butyllithium addition was completed, the solution was stirred at the reflux temperature for 30 minutes. Sulfur (1.6 g, 0.05 mol) was then added through the reflux condenser and the resulting solution was stirred at the reflux temperature for an additional 30 minutes.

The diethyl ether solution of N-methyl-3-chlorobenzenepropanamine, prepared above, was added to the 250 ml flask over a period of ten minutes. The resulting solution was heated until the liquid began to reflux and then stirred at that temperature for 45 minutes. The solution was cooled to room temperature (24° C.) and 50 ml of water were added. The organic layer was separated from the aqueous layer and extracted with 50 ml of a 1N hydrochloric acid solution. The extract was basified and then extracted with diethyl ether. The ether extract was washed with a saturated brine solution, dried over sodium carbonate, and the diethyl ether removed under reduced pressure to provide 7.0 g of an oil.

The oil was purified using preparative HPLC to provide 2.0 g of an oil. The oil was dissolved in diethyl ether and hydrochloric acid gas was passed through the solution for about 15 minutes. The diethyl ether was removed under reduced pressure and replaced with methylene chloride. Hexane was added and N-methyl-3-(2-thienylthio)benzenepropanamine hydrochloride (1.22 g) precipitated, which was recovered by filtration. m.p. = < 100° C.

Analysis calculated for $C_{14}H_{18}NS_2Cl$. Theory: C, 56.07; H, 6.05; N, 4.67; Found C, 55.83; H, 6.00; N, 4.62;

EXAMPLE 7

N-Methyl-3-[(5-methyl-2-thienyl)thio]benzenepropanamine hydrochloride

In an analogous manner to that described in Example 6, the title compound was prepared by reacting 12.0 g (0.055 mol) of N-methyl-3-chlorobenzenepropanamine hydrochloride, 4.36 g (0.055 mol of NaOH) of a 50%, by weight, sodium hydroxide solution, 4.9 g (0.05 mol) of 2-methylthiophene, 21 ml of a 1.6M solution of n-butyllithium dissolved in hexane, and 1.6 g (0.05 mol) of sulfur. The crude oil obtained was purified using preparative HPLC and then dissolved in diethyl ether. Hydrochloric acid gas was passed through the diethyl ether solution for about 15 minutes. Methylene chloride was added and 300 mg of N-methyl-3-[(5-methyl-2-thienyl)thio]benzenepropanamine hydrochloride precipitated, which were recovered by filtration. m.p. ≈ 100° C.

Analysis calculated for $C_{15}H_{20}NS_2Cl$; Theory: C, 57.39; H, 6.42; N, 4.46; Found: C, 57.10; H, 6.20; N, 4.71.

As noted above, the compounds of this invention are useful for inhibiting the uptake of serotonin. Therefore, another embodiment of the present invention is a method for inhibiting serotonin uptake in mammals which comprises administering to a mammal requiring increased neurotransmission of serotonin a pharmaceutically effective amount of a compound of the invention.

Compounds of the invention also have the ability to inhibit the uptake of norepinephrine. As such, yet another embodiment of this invention is a method for inhibiting norepinephrine uptake in mammals which comprises administering to a mammal requiring increased neurotransmission of norepinephrine a pharmaceutically effective amount of a compound of the invention.

The term "pharmaceutically effective amount", as used herein, represents an amount of a compound of the invention which is capable of inhibiting serotonin or norepinephrine uptake. The particular dose of compound administered according to this invention will of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular or intranasal routes. A typical daily dose will contain from about 0.01 mg/kg to about 20 mg/kg of the active compound of this invention. Preferred daily doses will be about 0.05 to about 10 mg/kg, ideally about 0.1 to about 5 mg/kg.

A variety of physiologic functions have been shown to be subject to influence by brain serotoninergic and norepinephrinergic neural systems. As such, the compounds of the present invention are believed to have the ability to treat a variety of disorders in mammals associated with these neural systems such as obesity, depression, alcoholism, pain, loss of memory, anxiety and smoking. Therefore, the present invention also provides methods of treating the above disorders at the rates set forth above for inhibiting serotonin and norepinephrine uptake in mammals.

The following experiment was conducted to demonstrate the ability of the compounds of the present invention to inhibit the uptake of serotonin and norepinephrine. This general procedure is set forth by Wong et al., in *Drug Development Research* 6:397–403 (1985).

Male Sprague-Dawley rats (110–150 g) from Harlan Industries (Cumberland, Id.) were fed a Purina Chow ad libitum for at least 3 days before being used in the studies. Rats were killed by decapitation. Whole brains were removed and dissected. Cerebral cortex was homogenized in 9 volumes of a medium containing 0.32M sucrose and 10 mM glucose. Crude synaptosomal preparations were isolated after differential centrifugation at 1,000 g for 10 min. and 17,000 g for 28 min. The final pellets were suspended in the same medium and kept in ice until use within the same day.

Synaptosomal uptake of $^3$H-serotonin($^3$H-5-hydroxytryptamine, $^3$H-5HT) and $^{14}$C-l-norepinephrine ($^{14}$C-NE) was determined as follows. Cortical synaptosomes (equivalent to 1 mg of protein) were incubated at 37° C. for 5 min in 1 ml of Krebs-bicarbonate medium containing also 10 mM glucose, 0.1 mM iproniazid, 1 mM ascorbic acid, 0.17 mM EDTA, 50$^3$H-5HT and 100 nM$^{14}$C-NE. The reaction mixture was immediately diluted with 2 ml of ice-chilled Krebs-bicarbonate buffer and filtered under vacuum with a cell harvester (Brandel, Gaithersburg, Md.). Filters were rinsed twice with approximately 5 ml of ice-chilled 0.9% saline and were transferred to a counting vial containing 10 ml of scintillation fluid (PCS, Amersham, Arlington Heights, Ill.). Radioactivity was measured by a liquid scintillation spectrophotometer. Accumulation of $^3$H-5HT and $^{14}$C-NE at 4° C. represented the background and was subtracted from all samples.

While all of the compounds of the invention inhibit the uptake of serotonin and norepinephrine to some degree, certain of the compounds possess a unique selectivity in that they block the uptake of one of the monoamines to a far greater extent than they do the uptake of the other monoamine. The results of the evaluation of the compounds of the present invention are set forth below in Table I. In the Table, columns 2–6 identify the structure of the compounds evaluated when taken with the formula set forth in the heading, and columns 7 and 8 provide the concentration of the test compound (at $10^{-9}$M) needed to inhibit 50% of serotonin (5HT) or norepinephrine, respectively (indicated in the Table as IC$_{50}$). The numbers in parentheses represent percent inhibition at 1000 nM for those compounds which failed to achieve 50% inhibition by that concentration.

TABLE I

INHIBITION OF 5HT AND NOREPINEPHRINE UPTAKE IN VITRO $$R-\overset{(O)_n}{\underset{R^1}{S}}-CH-CH_2-CH_2-N\overset{R^2}{\underset{R^3}{}}$$

| Compound of Example No. | R | n | R$^1$ | R$^2$ | R$^3$ | IC$_{50}$ (nM) 5HT | NE |
|---|---|---|---|---|---|---|---|
| 1 | 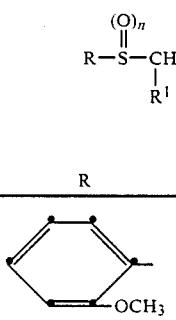 | 0 | 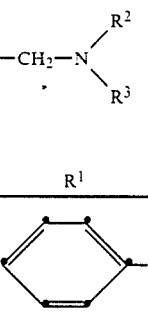 | H | CH$_3$ | 270 | 42 |
| 2 |  | 0 |  | H | CH$_3$ | 165 | 80 |
| 3 | 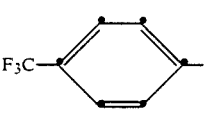 | 0 |  | H | CH$_3$ | 110 | (11) |
| 4 |  | 1 | 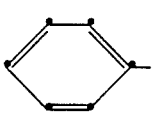 | H | CH$_3$ | (23) | (6) |

TABLE I-continued

INHIBITION OF 5HT AND NOREPINEPHRINE UPTAKE IN VITRO

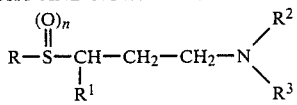

| Compound of Example No. | R | n | R¹ | R² | R³ | IC$_{50}$ (nM) 5HT | NE |
|---|---|---|---|---|---|---|---|
| 5 | F$_3$C-⟨phenyl⟩ | 2 | ⟨phenyl⟩ | H | CH$_3$ | (5) | (1) |
| 6 | ⟨thiophene⟩ | 0 | ⟨phenyl⟩ | H | CH$_3$ | 1000 | 48 |
| 7 | CH$_3$-⟨thiophene⟩ | 0 | ⟨phenyl⟩ | H | CH$_3$ | 1000 | 300 |

The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl-and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

| | Quantity (mg/capsule) |
|---|---|
| N—methyl-3-[(2-methoxyphenyl)thio]-benzenepropanamine hydrochloride | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

| | Quantity (mg/tablet) |
|---|---|
| N—methyl-3-[[4-(trifluoromethyl)phenyl]thio]benzenepropanamine hydrochloride | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components:

|  | Weight % |
| --- | --- |
| (+)-N—methyl-3-(2-thienylthio)benzene- propanamine hydrochloride | 0.25 |
| ethanol | 29.75 |
| Propellant 22 | 70.00 |
| (chlorodifluoromethane) |  |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| (−)-N—methyl-3-[(2-methylphenyl)thio] benzenepropanamine hydrochloride | 60 mg |
| --- | --- |
| starch | 45 mg |
| microcrystalline cellulose | 35 mg |
| polyvinylpyrrolidone | 4 mg |
| (as 10% solution in water) |  |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| N—methyl-3-[(5-methyl-2-thienyl)thio]- benzenepropanamine hydrochloride | 80 mg |
| --- | --- |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of active ingredient may be made as follows:

| (+)-N-methyl-3-[[4-trifluoromethyl)phenyl]- sulfinyl]benzenepropanamine hydrochloride | 225 mg |
| --- | --- |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| (−)-N—methyl-3-[(2-methoxyphenyl)thio]- benzenepropanamine hydrochloride | 50 mg |
| --- | --- |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| N—methyl-3-[(2-methylphenyl)thio]- benzenepropanamine hydrochloride | 100 mg |
| --- | --- |
| isotonic saline | 1000 ml |

The solution of the above ingredients is administered intravenously at a rate of 1 ml per minute to a subject suffering from depression.

We claim:

1. A compound of the formula $$R-S(O)_n-CH(R^1)-CH_2-CH_2-N(R^2)(R^3)$$

wherein:
R is phenyl, substituted phenyl, naphthyl, substituted naphthyl, thienyl, halothienyl, ($C_1$-$C_4$ alkyl)-substituted-thienyl, furanyl, halofuranyl, ($C_1$-$C_4$ alkyl)-substituted-furanyl, pyrrolyl, halopyrrolyl or ($C_1$-$C_4$ alkyl)-substituted-pyrrolyl;

$R^1$ is phenyl, substituted phenyl, $C_5$-$C_7$ cycloalkyl, thienyl, halothienyl, ($C_1$-$C_4$ alkyl)-substituted-thienyl, furanyl, pyridyl or thiazolyl;

$R^2$ and $R^3$ are each independently hydrogen or methyl;

n is 0, 1 or 2; and the pharmaceutically acceptable acid addition salts thereof.

2. A compound of claim 1 wherein R is phenyl, substituted phenyl, naphthyl, substituted naphthyl, thienyl or ($C_1$-$C_4$ alkyl)-substituted-thienyl and $R^1$ is phenyl.

3. A compound of claim 2 wherein n is 0.

4. A compound of claim 3 wherein R is phenyl; phenyl substituted with methyl, methoxy or trifluoromethyl; thienyl; or methyl-substituted-thienyl.

5. A compound of claim 4 wherein $R^2$ is hydrogen and $R^3$ is methyl.

6. A compound of claim 5, said compound being N-methyl-3-[(2-methylphenyl)thio]benzenepropanamine or a pharmaceutically acceptable acid addition salt thereof.

7. A compound of claim 5, said compound being N-methyl-3-[(2-methoxyphenyl)thio]benzenepropanamine or a pharmaceutically acceptable acid addition salt thereof.

8. A compound of claim 5, said compound being N-methyl-3-[[4-(trifluoromethyl)phenyl]thio]benzenepropanamine or a pharmaceutically acceptable acid addition salt thereof.

9. A compound of claim 5, said compound being N-methyl-3-(2-thienylthio)benzenepropanamine or a pharmaceutically acceptable acid addition salt thereof.

10. A method for inhibiting serotonin uptake in mammals which comprises administering to a mammal requiring increased neurotransmission of serotonin a pharmaceutically effective amount of a compound of claim 1.

11. A method of claim 10 wherein the compound is N-methyl-3-[(2-methylphenyl)thio]benzenepropanamine or a pharmaceutically acceptable acid addition salt thereof.

12. A method of claim 10 wherein the compound is N-methyl-3-[(2-methoxyphenyl)thio]benzenepropanamine or a pharmaceutically acceptable acid addition salt thereof.

13. A method of claim 10 wherein the compound is N-methyl-3-[[4-(trifluoromethyl)phenyl]thio]benzenepropanamine or a pharmaceutically acceptable acid addition salt thereof.

14. A method for inhibiting norepinephrine uptake in mammals which comprises administering to a mammal requiring increased neurotransmission of norepinephrine a pharmaceutically effective amount of a compound of claim 1.

15. A method of claim 14 wherein the compound is N-methyl-3-[(2-methylphenyl)thio]benzenepropanamine or a pharmaceutically acceptable acid addition salt thereof.

16. A method of claim 14 wherein the compound is N-methyl-3-[(2-methoxyphenyl)thio]benzenepropanamine or a pharmaceutically acceptable acid addition salt thereof.

17. A method of claim 14 wherein the compound is N-methyl-3-(2-thienylthio)benzenepropanamine or a pharmaceutically acceptable acid addition salt thereof.

18. A method of treating depression in humans comprising administering to a human suffering from depression an effective antidepressant dose of a compound of claim 1.

19. A method of treating anxiety in a human comprising administering to a human suffering from anxiety an effective antianxiety dose of a compound of claim 1.

20. A method of treating obesity in humans comprising administering to a human suffering from obesity an effective antiobesity dose of a compound of claim 1.

21. A method of suppressing the desire of humans to smoke comprising administering to a human in need of such suppression an effective dose to relieve the desire to smoke of a compound of claim 1.

22. A method of suppressing the desire of humans to consume alcohol comprising administering to a human in need of such suppression an effective dose to relieve the desire to consume alcohol of a compound of claim 1.

23. A pharmaceutical formulation comprising a compound of claim 1 and a pharmaceutically acceptable carrier, diluent or excipient therefor.

24. A formulation of claim 23 wherein the compound is N-methyl-3-[(2-methylphenyl)thio]benzenepropanamine or a pharmaceutically acceptable acid addition salt thereof.

25. A formulation of claim 23 wherein the compound is N-methyl-3-[(2-methoxyphenyl)thio]benzenepropanamine or a pharmaceutically acceptable acid addition salt thereof.

26. A formulation of claim 23 wherein the compound is N-methyl-3-[[4-(trifluoromethyl)phenyl]thio]benzenepropanamine or a pharmaceutically acceptable acid addition salt thereof.

27. A formulation of claim 23 wherein the compound is N-methyl-3-(2-thienylthio)benzenepropanamine or a pharmaceutically acceptable acid addition salt thereof.

* * * * *